United States Patent
Bharatiya et al.

(10) Patent No.: US 11,150,648 B2
(45) Date of Patent: Oct. 19, 2021

(54) OVERHEAD POWER CABLE DETECTION AND AVOIDANCE

(71) Applicant: Deere & Company, Moline, IL (US)

(72) Inventors: Paresh Bharatiya, Pune (IN); Shruti Dev, Pune (IN)

(*) Notice: Subject to any disclaimer, the term of this patent is extended or adjusted under 35 U.S.C. 154(b) by 333 days.

(21) Appl. No.: 15/943,849

(22) Filed: Apr. 3, 2018

(65) Prior Publication Data

US 2019/0302762 A1   Oct. 3, 2019

(51) Int. Cl.
| | | |
|---|---|---|
| *G05D 1/00* | (2006.01) | |
| *B60Q 1/50* | (2006.01) | |
| *G01N 33/00* | (2006.01) | |
| *G01R 19/25* | (2006.01) | |
| *G05B 15/02* | (2006.01) | |
| *A01M 7/00* | (2006.01) | |

(52) U.S. Cl.
CPC .......... *G05D 1/0055* (2013.01); *A01M 7/005* (2013.01); *A01M 7/0075* (2013.01); *A01M 7/0089* (2013.01); *B60Q 1/50* (2013.01); *G01N 33/0039* (2013.01); *G01R 19/2513* (2013.01); *G05B 15/02* (2013.01); *G05D 1/0011* (2013.01)

(58) Field of Classification Search
CPC .............. G05D 1/0055; G05D 1/0011; G01N 33/0039; G01N 33/0009; G01R 19/2513; G05B 15/02; A01M 7/0089; A01M 7/0075; A01M 7/005; B60Q 1/50
USPC .......................................................... 701/50
See application file for complete search history.

(56) References Cited

U.S. PATENT DOCUMENTS

| | | | | |
|---|---|---|---|---|
| 4,649,375 A | * | 3/1987 | Duppong ............ | G01R 19/145 212/280 |
| 5,859,597 A | * | 1/1999 | Cornelio .............. | G01R 29/085 324/207.2 |
| 6,104,305 A | * | 8/2000 | Beckmann ........... | B66C 15/065 340/685 |
| 6,133,841 A | * | 10/2000 | Beckmann ........... | B66C 15/065 212/280 |
| 6,252,513 B1 | * | 6/2001 | Beckmann ........... | B66C 15/065 212/280 |
| 6,600,426 B1 | * | 7/2003 | Sacks ....................... | B60P 1/00 340/664 |

(Continued)

FOREIGN PATENT DOCUMENTS

WO         02086519 A1    10/2002

OTHER PUBLICATIONS

Whitmore, Frank C., and Robert L. Durfee. Determination of Coronal Ozone Production by High Voltage Power Transmission Lines. U.S. Environmental Protection Agency Distributed by National Technical Information Service, Springfield, VA., 1973. (Year: 1973).*

(Continued)

*Primary Examiner* — Angelina Shudy
*Assistant Examiner* — Mohamed Abdo Algehaim
(74) *Attorney, Agent, or Firm* — Joseph R. Kelly; Kelly, Holt & Christenson PLLC

(57) ABSTRACT

A mobile machine includes a sensor that generates a sensor signal indicative of ozone gas concentration. A power cable proximate the mobile machine, is identified based on the sensor signal. An avoidance action, is identified in response to determining that the power cable is proximate the mobile machine, and a control signal is generated based on the identified avoidance action.

19 Claims, 9 Drawing Sheets

(56) References Cited

U.S. PATENT DOCUMENTS

| | | | |
|---|---|---|---|
| 6,660,426 B2 | 7/2003 | Sacks et al. | |
| 7,369,045 B2* | 5/2008 | Hansen | H02J 13/0075 333/24 R |
| 8,184,015 B2 | 5/2012 | Lilien et al. | |
| 8,477,027 B2* | 7/2013 | Givens | B66C 13/44 340/538 |
| 9,756,773 B1* | 9/2017 | Barbosa | A01B 79/005 |
| 9,766,105 B2* | 9/2017 | Ni | B05B 12/008 |
| 9,886,803 B2* | 2/2018 | Oswald | B66C 13/18 |
| 10,067,170 B2* | 9/2018 | Olson | G01R 29/085 |
| 10,219,506 B2* | 3/2019 | Ni | A01M 7/005 |
| 10,391,503 B2* | 8/2019 | Hanna | B05B 1/20 |
| 2005/0286190 A1* | 12/2005 | Rostron | G01R 15/142 361/65 |
| 2006/0125469 A1* | 6/2006 | Hansen | H02J 13/0075 340/538.16 |
| 2008/0167754 A1* | 7/2008 | McAllister | G01N 33/004 700/293 |
| 2010/0061885 A1* | 3/2010 | Harley | G01N 21/85 422/3 |
| 2010/0200668 A1* | 8/2010 | Hahn | A01C 23/007 239/1 |
| 2010/0206787 A1* | 8/2010 | Rozenberg | G01N 21/33 210/96.1 |
| 2010/0214094 A1* | 8/2010 | Givens | B66C 13/44 340/539.17 |
| 2011/0153169 A1* | 6/2011 | Peterson | A01M 7/0075 701/50 |
| 2013/0033258 A1* | 2/2013 | Parr | G01B 7/14 324/207.22 |
| 2013/0325242 A1* | 12/2013 | Cavender-Bares | A01C 21/002 701/25 |
| 2016/0368011 A1* | 12/2016 | Feldhaus | A01M 7/0089 |
| 2017/0107090 A1* | 4/2017 | Mondal | B66F 17/006 |
| 2017/0118915 A1* | 5/2017 | Middelberg | A01B 69/008 |
| 2017/0131718 A1* | 5/2017 | Matsumura | G05D 1/02 |
| 2017/0227677 A1* | 8/2017 | Godard | G01L 5/107 |
| 2017/0285092 A1* | 10/2017 | Moore | G05D 1/0094 |
| 2017/0359515 A1* | 12/2017 | Harris | G06K 9/00 |
| 2018/0027727 A1* | 2/2018 | Leeb | A01M 7/0057 |
| 2018/0157250 A1* | 6/2018 | Barnickel | H04L 67/12 |
| 2018/0196435 A1* | 7/2018 | Kunzi | G05D 1/0088 |
| 2018/0239991 A1* | 8/2018 | Weller | G06K 9/00651 |
| 2018/0284788 A1* | 10/2018 | Remboski | B66F 17/006 |
| 2018/0325012 A1* | 11/2018 | Ferrari | A01B 69/001 |
| 2019/0009285 A1* | 1/2019 | Zimmerman | A01M 7/0042 |
| 2019/0090472 A1* | 3/2019 | Crinklaw | A01B 69/008 |
| 2019/0205609 A1* | 7/2019 | Taveira | G05D 1/0202 |
| 2019/0213691 A1* | 7/2019 | Kaarnametsa | A01G 23/08 |
| 2019/0221095 A1* | 7/2019 | Bonnard | G08B 17/117 |
| 2019/0226856 A1* | 7/2019 | Ghannam | G07C 5/008 |
| 2020/0062565 A1* | 2/2020 | Cousins | B66C 15/065 |

OTHER PUBLICATIONS

White, Richard M, et al. "Atmospheric Sensors and Energy Harvesters on Overhead Power Lines." Sensors (Basel, Switzerland), MDPI, Jan. 3, 2018, www.ncbi.nlm.nih.gov/pubmed/29301354. (Year: 2018).*

European Search Report issued in counterpart application No. 19166701.3 dated Aug. 21, 2019. (5 pages).

Ozone concentration variations near high-voltage transmission lines, https://www.tandfonline.com/doi/pdf/10.3846/1648-6897.2009.17.28-35 Published online: Oct. 14, 2010. 9 pages.

Fern et al. Field Investigation of Ozone Adjacent to High Voltage Transmission Lines, Document No. 2004. Accessed Apr. 2, 2018. 13 pages.

* cited by examiner

OVERHEAD POWER CABLE DETECTION AND AVOIDANCE

FIELD OF THE DESCRIPTION

The present description relates to the use of mobile machines in agricultural and other applications. More specifically, the present description relates to the use of sensors in detecting hazards and controlling mobile machines to avoid the hazards.

BACKGROUND

There are a wide variety of different types of equipment, such as construction equipment, turf care equipment, agricultural equipment, and forestry equipment. These types of equipment are often large and it can be difficult for an operator to be aware of all things surrounding the machine.

Agricultural equipment can include a wide variety of machines such as harvesters, sprayers, and planters, among others. Agricultural equipment can be operated by an operator, and have many different mechanisms that are controlled by the operator in performing an operation. The equipment may have multiple different mechanical, electrical, hydraulic, pneumatic, electromechanical (and other) subsystems, some or all of which can be controlled, at least to some extent, by the operator.

Current systems may experience difficulty in acquiring information and utilizing the acquired information to control machines to avoid hazards at a worksite. These difficulties can be exacerbated because of the complex nature of the operations performed by these machines, including movement over complex terrain and because of environmental conditions at agricultural worksites, as well as difficulty in achieving safe and efficient maneuverability of large machinery.

The discussion above is merely provided for general background information and is not intended to be used as an aid in determining the scope of the claimed subject matter.

SUMMARY

A mobile machine includes a sensor that generates a sensor signal indicative of ozone gas concentration. Power cable detection logic receives the sensor signal and, based on the received sensor signal, determines that a power cable is proximate the mobile machine. Avoidance decision logic identifies an avoidance action in response to determining that the power cable is proximate the mobile machine, and a control signal generator generates a control signal based on the avoidance action.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

A wide variety of different agricultural operations can be performed within a worksite. Some example agricultural operations include preparing a worksite, harvesting a planted material, and applying a fluid or other material to the worksite, among others. Many such agricultural operations utilize machinery that can perform a variety of functions.

Agricultural machines (also referred to herein as a machine, a mobile machine, and a vehicle) often have a wide variety of sensors that sense a variety of different variables such as machine operating parameters, worksite characteristics, environmental parameters, etc. Sensor signals are communicated over a controller area network (CAN) bus (or another network, such as an Ethernet network, WiFi etc.) to various systems that process the sensed variables to generate output signals (such as control signals or other outputs) based on the sensed variables.

However, it can be difficult for some current systems to not only obtain accurate and valuable sensed variables, but to also analyze the sensed variables along with other worksite information to produce meaningful results. For instance, it can be difficult for some current systems to predict and avoid hazardous conditions at a worksite.

A particular hazardous condition can be present when machinery is operating at a worksite having overhead, electrical power cables. Overhead power cables can be spread out across the worksite to transmit high voltage electricity. It can be difficult for an operator to see the power cables from within a cab of the mobile machine, and it can also be difficult to control the machine to avoid contact with the power cables or their supports. This problem can be exacerbated when operating large or bulky machinery. For instance, a mobile spraying machine can include an elongated boom that is raised in a deployed position some height off of the ground. The boom can be moved between the deployed position and a travel position by folding or articulating it. Sometimes, arm portions of the boom are folded upwardly, making them extend into the air even higher. Thus, the boom can be at an increased risk for contacting the power cables. If the boom, or any other part of the mobile machine for that matter, contacts a power cable or its support, it can be very dangerous for both the mobile machine and its operator.

The present description thus discloses detecting power cables at a worksite and automatically implementing a corrective action to avoid the hazard. As will be discussed in further detail below, one example system addresses these challenges by using sensors to detect an active power cable based on a sensed presence of ozone gas in the atmosphere near the mobile machine, and by subsequently controlling the mobile machine to avoid the detected power cable.

Figure 1A:
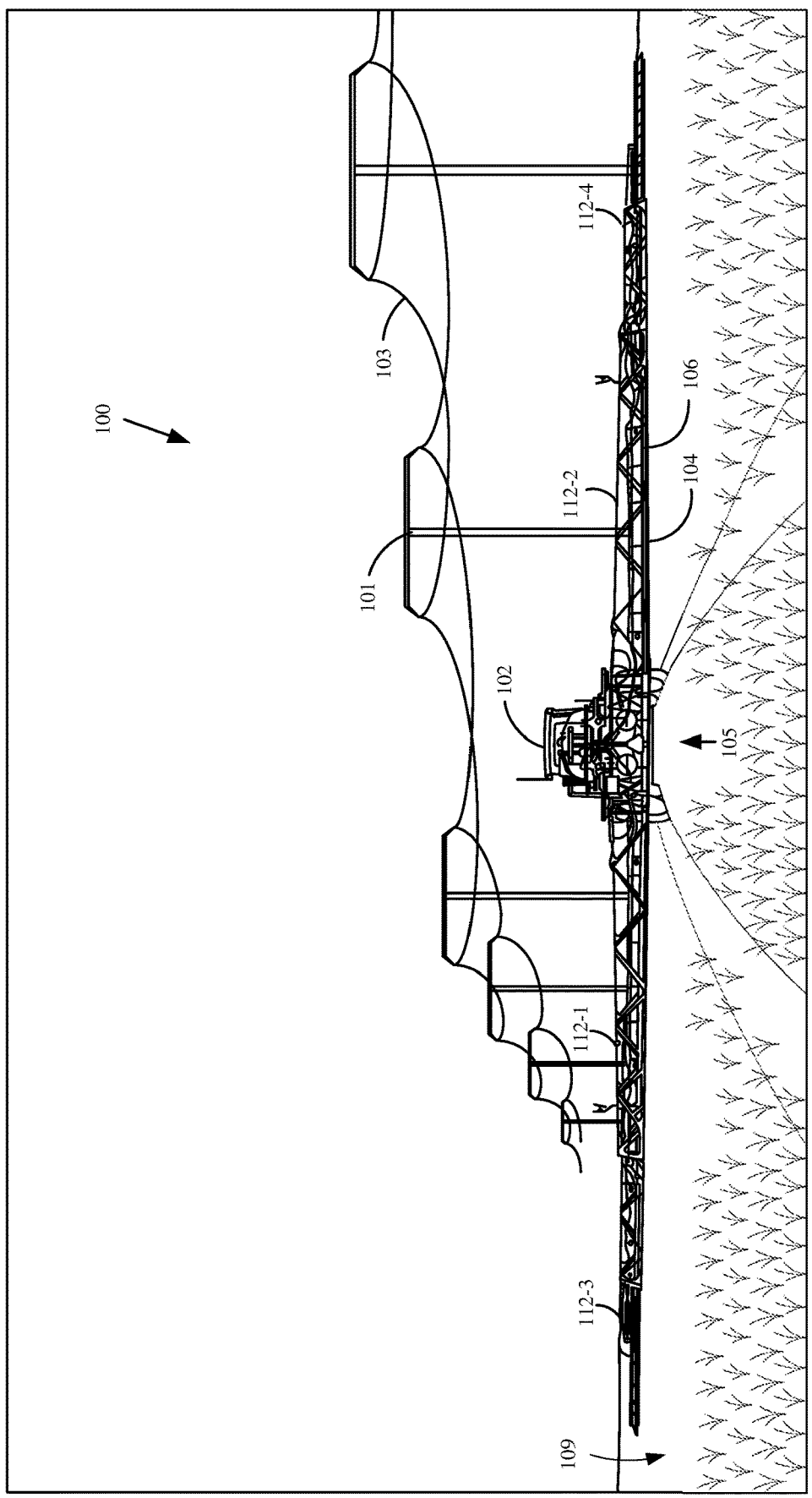
FIG. 1A is a pictorial illustration of a worksite with a mobile machine using an overhead power cable avoidance system, showing one example configuration of a boom in a deployed position.

FIG. 1A is a pictorial illustration of a worksite 100 with a mobile machine 102 using an overhead power cable avoidance system (discussed below), having one example configuration of a boom 104 in a deployed position. Mobile machine 102 generally operates to perform one or more operations at worksite 100. In the illustrated example, mobile machine 102 is a self-propelled sprayer. Mobile machine 102 can travel in the direction generally indicated by arrow 105 to, for example, spray crops at worksite 100. Mobile machine 102 illustratively includes a boom 104 having elongate arms 112-1, 112-2, 112-3 and 112-4 (collectively—arm(s) 112). As is discussed below, arm portions 112-1 and 112-3 may be coupled to one another by an articulating joint. Arm portions 112-2 and 112-4 may be as well. One or more sprayer nozzles(s) (positioned generally along boom 104 on a lower portion and generally designated by numeral 106) are disposed along elongate arms 112 and are configured to dispense a material to worksite 100. For instance, sprayer nozzles(s) 106 can be operably coupled to a pump that provides fluid, from a fluid source, to sprayer nozzles 106. Nozzles 106 spray the fluid onto the field.

FIG. 1A generally shows boom 104 in a deployed position. In the deployed position, elongate arms 112-1 and 112-2 are generally positioned in a horizontal orientation, such that boom 104 is substantially parallel to a ground surface 109. In the deployed position, boom 104 is generally wider than mobile machine 102. In one example, boom 104 is movable to adjust its length, and can extend in excess of 120 feet in a fully deployed position. In this example, each of arms 112-1 and 112-2 can extend in excess of approximately 55 feet in a direction beyond a width of mobile machine 102. As shown, each of the arms 112-1 and 112-2 extend in excess of 55 feet, in a generally horizontal orientation, generally perpendicular to the direction of travel indicated by arrow 105. Boom 104 thus includes features that allow an operator to spray over a wide area of ground surface 109 during each pass that mobile machine 102 makes across worksite 100.

FIG. 1A also shows power cables 103 supported by supports 101. Power cables 103 generally carry high voltage electricity. Sometimes, power cables 103 and supports 101 can be in a vicinity of, or even within the boundaries of, worksite 100. In some examples, it can be difficult for an operator to observe where power cables 103 and supports 101 are positioned relative to mobile machine 102, and more specifically where they are positioned relative to boom 104.

During operation, boom 104 can be moved either automatically or semi-automatically, such as in response to a user input or by controlling hydraulic actuators coupled to arms 112, such that arms 112 move through a wide variety of different positions. For instance, boom 104 can be moved between the deployed position shown in FIG. 1A and a travel position shown in FIG. 1C. While the deployed position shown in FIG. 1A is particularly useful while spraying worksite 100, it can be difficult to transport mobile machine 102 across long distances or on roadways when arms 112 are elongated in this position.

Figure 1B:
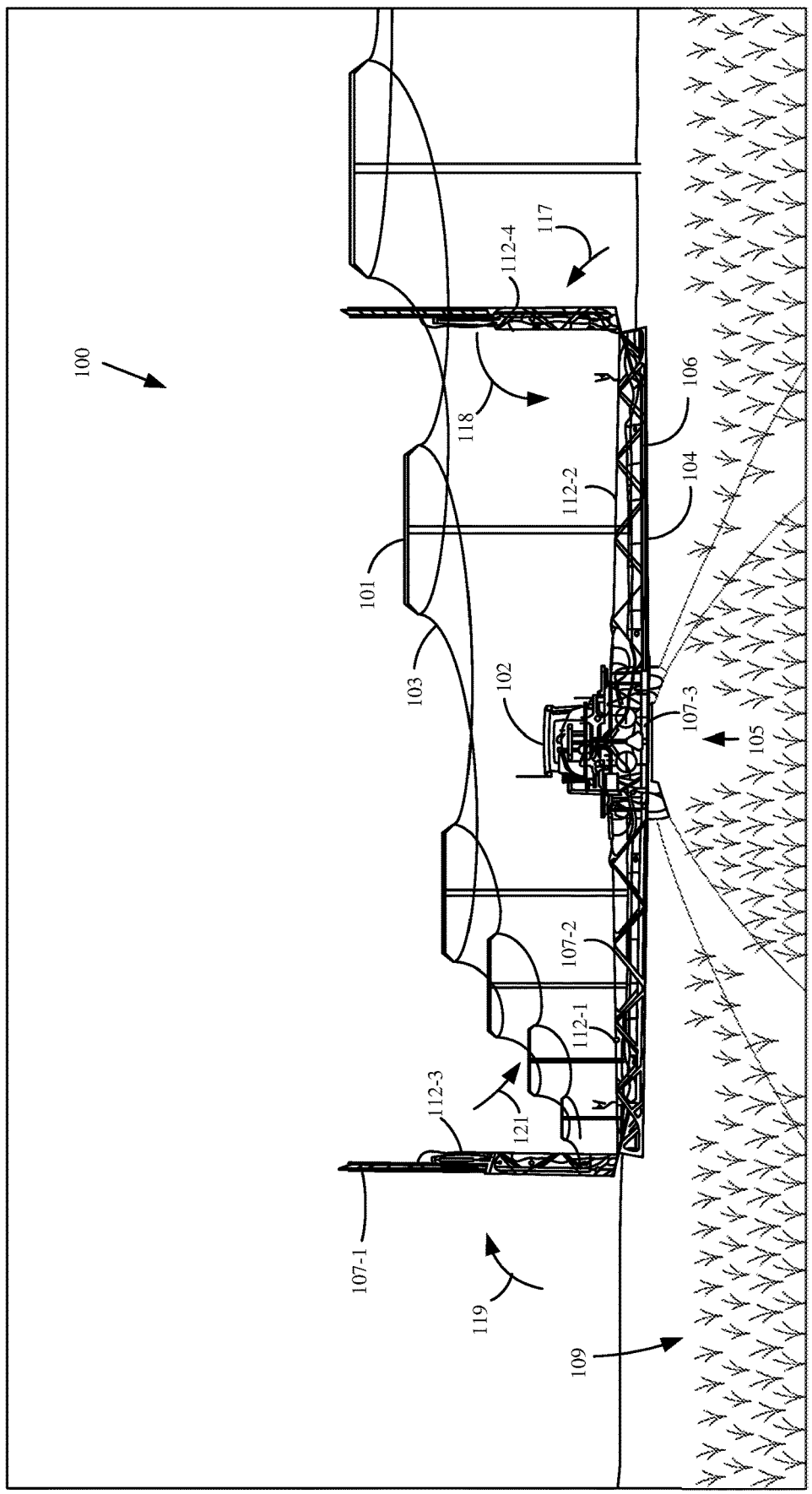
FIG. 1B is a pictorial illustration of the mobile machine using the overhead power cable avoidance system illustrated in FIG. 1A, showing one example configuration of a boom between a deployed position and a travel position.
Figure 1C:
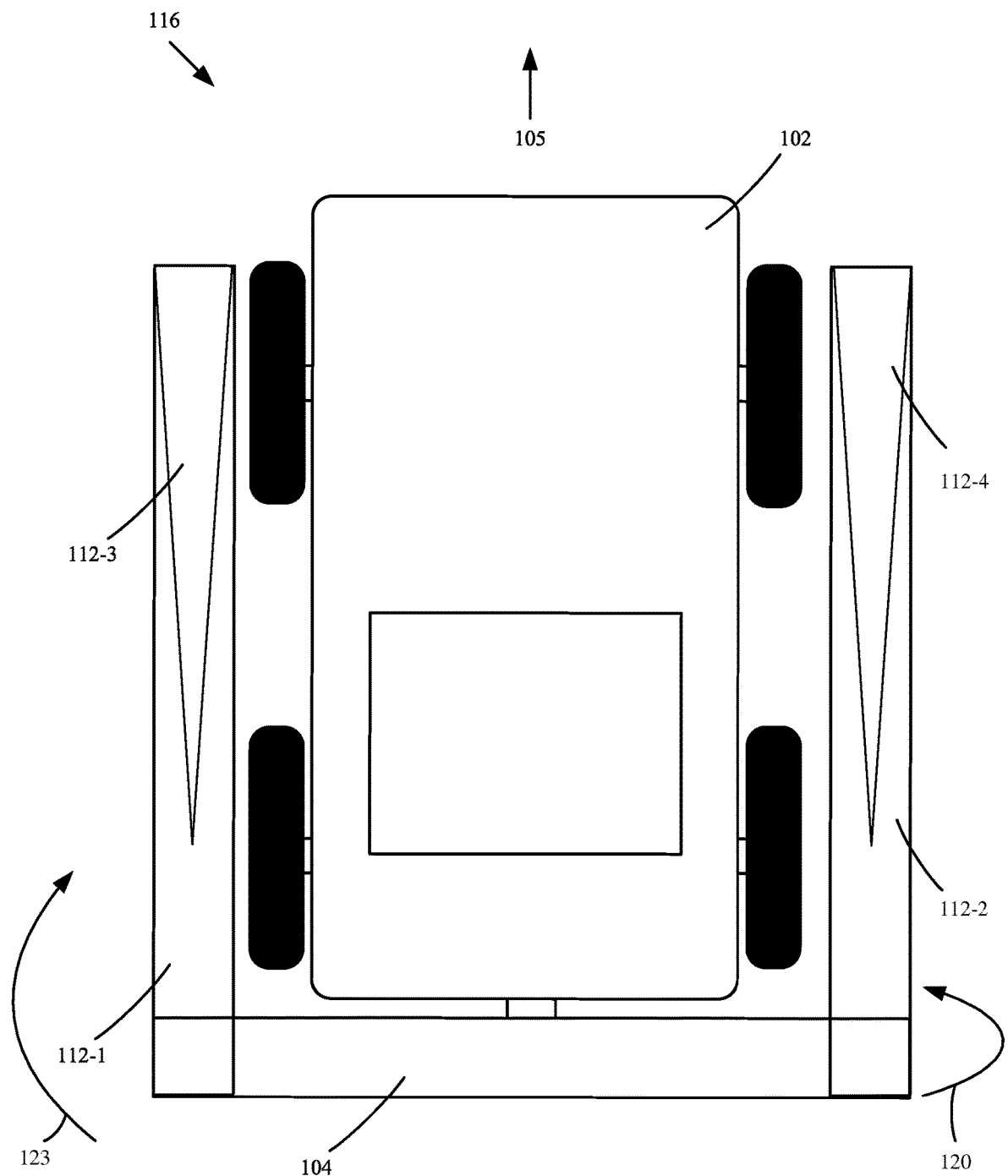
FIG. 1C is a pictorial illustration of an overhead view of the mobile machine, using the overhead power cable avoidance system illustrated in FIG. 1A, showing one example configuration of a boom in a travel position.

FIG. 1B is a pictorial illustration of mobile machine 102 in which boom 104 is in an intermediate position between the deployed position (FIG. 1A) and the travel position (FIG. 1C). Arm portions 112-3 and 112-4 generally indicate portions of boom 104 that are less proximate to mobile machine 102, relative to arms portions 112-1 and 112-2, which are more proximate to mobile machine 102. Arm portions 112-3 and 112-4 can each be moved independently of arm portions 112-1 and 112-2, respectively. In the example shown in FIG. 1B, to begin moving boom 104 to the travel position (shown in FIG. 1C), arm portions 112-3 and 112-4 are folded upwards, in the directions indicated by arrows 117 and 119 into a generally vertical orientation, so they are generally perpendicular to arm portions 112-1 and 112-2. In this position, arm portions 112-3 and 112-4 extend vertically beyond the height of mobile machine 102.

FIG. 1C is a pictorial illustration of an overhead view 116 of mobile machine 102, in which boom 104 is in a travel position. From the position shown in FIG. 1B, arm portions 112-3 and 112-4 can be subsequently folded down, generally towards ground surface 109, in the direction shown by arrows 118 and 121, so they are generally folded onto, and parallel with, arm portions 112-1 and 112-2. Then, arm portions 112-1 and 112-2 can be moved inwards towards mobile machine 102, so they are generally parallel to the direction of travel indicated by arrow 105. For example, FIG. 1C indicates this movement at reference numeral 120 and 123. Overhead view 116 thus illustratively shows arms portions 112-3 and 112-4 folded downwards and arm portions 112-1 and 112-2 folded inwards, so that arms 112 are less elongated (e.g., less wide) than when in the deployed position shown in FIG. 1A.

FIGS. 1A-1C therefore show one example of how boom 104 can be controlled to move through a series of positions that orient arms 112 in the most appropriate position for an operation being performed by mobile machine 102 (e.g., spraying operation vs. travel operation, etc.). However, moving arms 112 (e.g., changing their length, changing their orientation to machine 102, etc.) can sometimes make it even more difficult for an operator to observe where power cables 103 and supports 101 are positioned relative to boom 104. For example, an operator might attempt to move boom 104 between the deployed position and the travel position when mobile machine 102 is near overhead power cables 103. If overhead power cables 103 are not detected, as arm portions 112-3 and 112-4 are folded upwards vertically (for example), they might be at an increased risk of contacting power cables 103. Of course, it is noted that other movements of arms 112 can place boom 104 at an increased risk of contacting power cables 103 as well. Those discussed with respect to FIGS. 1A-1C are examples only.

Also, the present discussion proceeds with respect to a boom on a mobile machine. However, it will be appreciated that the same discussion can just as easily be had with respect to any mobile machine that has a mechanical assembly that can extend from, and retract toward, the mobile machine, such as a combine harvester that has an auger and spout that can swing away from the machine for unloading, among a wide a variety of other machines.

Figure 2:
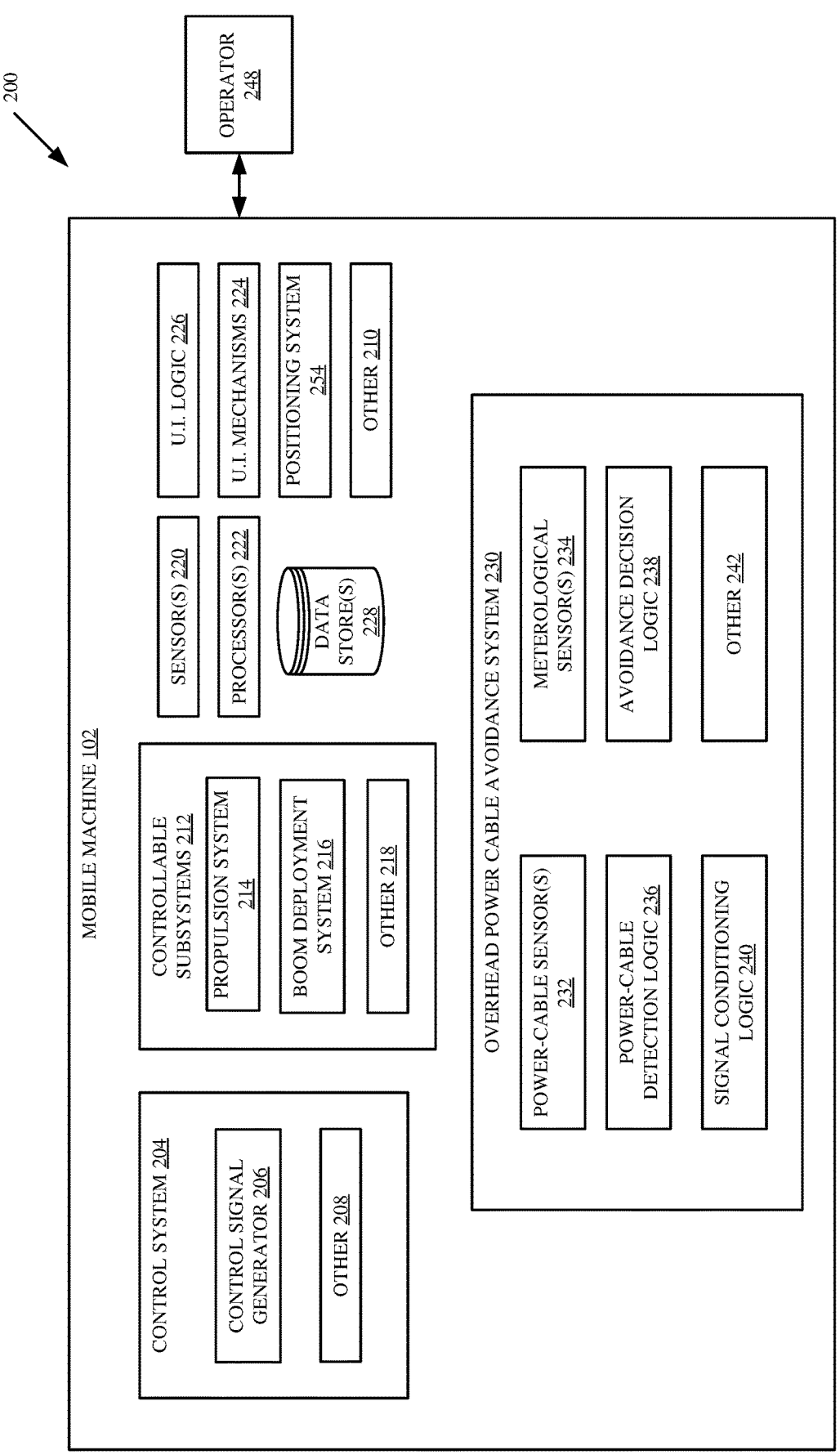
FIG. 2 is a block diagram of one example of a computing architecture that includes the overhead power cable avoidance system discussed with respect to FIGS. 1A-1C.

FIG. 2 is a block diagram of one example of a computing architecture 200 that includes an overhead power cable avoidance system 230 that can be used on mobile machine 102. Computing architecture 200 illustratively includes mobile machine 102 having overhead power cable avoidance system 230 and an operator 248. Prior to discussing features of overhead power cable avoidance system 230 in detail, a brief overview of computing architecture 200 and mobile machine 102 will first be provided.

Mobile machine 102 illustratively includes a control system 204, controllable subsystems 212, sensor(s) 220, processor(s) 222, user interface mechanisms 224, user interface logic 226, data stores(s) 228, and a positioning system 254, among other items 210. While the present description will primarily focus on an example in which mobile machine 102 includes a mobile spraying machine that performs spraying operations, it is noted that mobile machine 102 can include any of a wide variety of different machines (and it can include any and/or all of the features of mobile machine 102 as described above with respect to FIG. 1).

User interface mechanisms 224 can include one or more display devices, one or more audio devices, one or more haptic feedback devices, and other items, such as a steering wheel, joysticks, pedals, levers, buttons, keypads, etc. In one example, mobile machine 102 uses user interface logic 226 to detect user interaction with user interface mechanisms 224 and to generate signals indicative of this to other items. It can also use user interface logic 226 to generate outputs on user interface mechanisms 224. For instance, user interface logic 226 can generate operator interface displays having actuators (buttons, icons, etc.) for display on a user interface device and for interaction by operator 248. Operator 248 can interact with the actuators to control and manipulate mobile machine 102.

Sensor(s) 220 can generate a wide variety of different sensor signals representing a wide variety of different sensed variables. For instance, sensor(s) 220 can generate signals indicative of slope angle, soil moisture, proximity, acceleration, hydraulic actuator movement or position, a geographic location (e.g., where sensors 220 include a global positioning system (GPS) receiver or other positioning system), among others.

Positioning system 254 illustratively generates one or more signals indicative of a position of mobile machine 102 at any given time during an operation. Generally, positioning system 254 receives sensor signals from one or more sensor(s) 220, such as a GPS receiver, a dead reckoning system, a LORAN system, or a wide variety of other systems or sensors, to determine a position of mobile machine 102 across worksite 100. Positioning system 254 can also access data store(s) 228 to retrieve stored positioning information that indicates positions of mobile machine 102 in performing historical operations, as well as the paths and/or patterns of travel of mobile machine 102 during performance of the historical operations.

Control system 204 illustratively includes a control signal generator 206, among others things 208. Control signal generator 206 generates control signals for controlling a variety of different controllable subsystems 212, based on sensor signals generated by sensors 220 (and/or sensor(s) 232 and 234), based on user inputs received through user interface mechanisms 224 and detected via user interface logic 226, based on positioning information obtained from positioning system 254, and/or it can generate control signals in a wide variety of other ways as well.

Controllable subsystems 212 illustratively include a propulsion and steering system 214, and a boom deployment system 216, among other items 218. Propulsion and steering system 214 generally includes an engine that drives ground engaging wheels or tracks via a powertrain mechanism and steering actuators to control the direction of travel. Boom deployment system 216 generally includes any hydraulic or other actuator mechanisms that control movement of a boom 104 between a travel position and a deployed position. For instance, boom deployment system 216 can drive movement of one or more arms 112 through various different positions, such as the positions shown in FIGS. 1A-1C.

Overhead power cable avoidance system 230 illustratively includes power cable sensor(s) 232, meteorological sensor(s) 234, power cable detection logic 236, avoidance decision logic 238, and signal conditioning logic 240, among other items 242. Overhead power cable avoidance system 230 is generally configured to receive sensor signals from sensors 232, detect a presence of overhead power cables 103 based on the sensor signals, and implement an avoidance action that automatically or semi-automatically controls mobile machine 102 to avoid contact between mobile machine 102 (including boom 104) and overhead power cables 103.

Power cable sensor(s) 232 include one or more sensors, disposed on or near mobile machine 102, configured to generate a sensor signal indicative of the presence of an active power cable 103. When power cable 103 transmits high voltage electricity, the atmospheric air near the cable is ionized to generate ozone ($O_3$). Sensor(s) 232 are generally disposed at various positions on arm(s) 112 to generate sensor signals indicative of $O_3$ concentration within several meters of boom 104. For instance, power cable sensor(s) 232 include one or more ozone sensors that generate a sensor signal indicative a measured amount of $O_3$, in parts-per-billion (ppb), in a region of atmosphere near sensor(s) 232. That is, by way of example, sensor(s) 232 can generate sensor signals indicative of $O_3$ in a concentration range from 10-1000 ppb.

It can be difficult to utilize raw, unconditioned sensor signals generated by power-cable sensor(s) 232 to accurately detect presence of a power cable. For instance, environmental conditions such as wind speed, temperature, and humidity, among others, might influence the sensed values of $O_3$ in the atmosphere. Meteorological sensors 234 thus include one or more sensors, disposed on or near mobile machine 102, that are configured to generate a sensor signal indicative of a meteorological parameter, such as temperature, wind speed, relative humidity, and relative pressure, among other parameters. In one example, sensor signals generated by meteorological sensor(s) 234 can be used in conjunction with sensor signals generated by power cable sensor(s) 222 to more accurately determine the presence of power cable 103.

Signal conditioning logic 240 is generally configured to condition or adjust sensor signals, such as signals generated by power-cable sensor(s) 232, to generate a measured value indicating $O_3$ concentration. For instance, signal conditioning logic 240 can condition sensor signals that indicate $O_3$, based on sensor signals generated by meteorological sensor(s) 234. As an example, signal conditioning logic 240 can apply a coefficient to sensed signals indicating $O_3$, based on a sensed meteorological parameter such as wind speed and/or wind direction, thereby accommodating for effects that environmental conditions have on measured values of $O_3$ in the atmosphere.

Power cable detection logic 236 can receive a wide variety of inputs, such as sensor signals generated by power cable sensor(s) 232 and meteorological sensor(s) 234, conditioned signals from signal conditioning logic 240, and inputs from positioning system 254, among other inputs, to detect presence of power cable 103 at worksite 100. Based on the inputs received, power cable detection logic 236 can determine whether a measured amount of $O_3$ is present in the atmosphere. It can then determine whether this measured amount indicates that power cable 103 is near mobile machine 102, and, if so, it can determine a specific distance between mobile machine 102 and overhead power cable 103. For example, power cable detection logic 236 can determine that there is a concentration of 100 ppb of $O_3$ near boom 104 on mobile machine 102. Power cable detection logic 236 can compare the sensed concentration of $O_3$ to a reference value. A reference value can include a pre-defined amount or concentration of $O_3$, or it can include an amount or concentration of $O_3$ that is determined from a sensor signal generated by a reference sensor (e.g., a power cable sensor 232 positioned at a reference sensing position). Power cable detection logic 236 can then generate an output indicating whether a power cable is detected, as well an output indicating a position of the detected power cable relative to a portion of mobile machine 102, such as arms 112 of boom 104.

Avoidance decision logic 238 is generally configured to identify an avoidance action to be implemented by mobile machine 102 when logic 236 has determined that a power cable has been detected. Avoidance decision logic 238 can select an avoidance action, from a plurality of available avoidance actions, based at least in part on the output generated by power cable detection logic 236. In response to receiving an output indicating the presence of a power cable, avoidance decision logic 238 can select an action to be automatically or semi-automatically implemented by mobile machine 102 for avoiding contact between mobile machine 102 and power cables 103 and/or supports 101. Of course, if no power cable is detected, the avoidance decision that is selected can simply be to have mobile machine 102 continue performing a current operation, as is.

Figure 3:
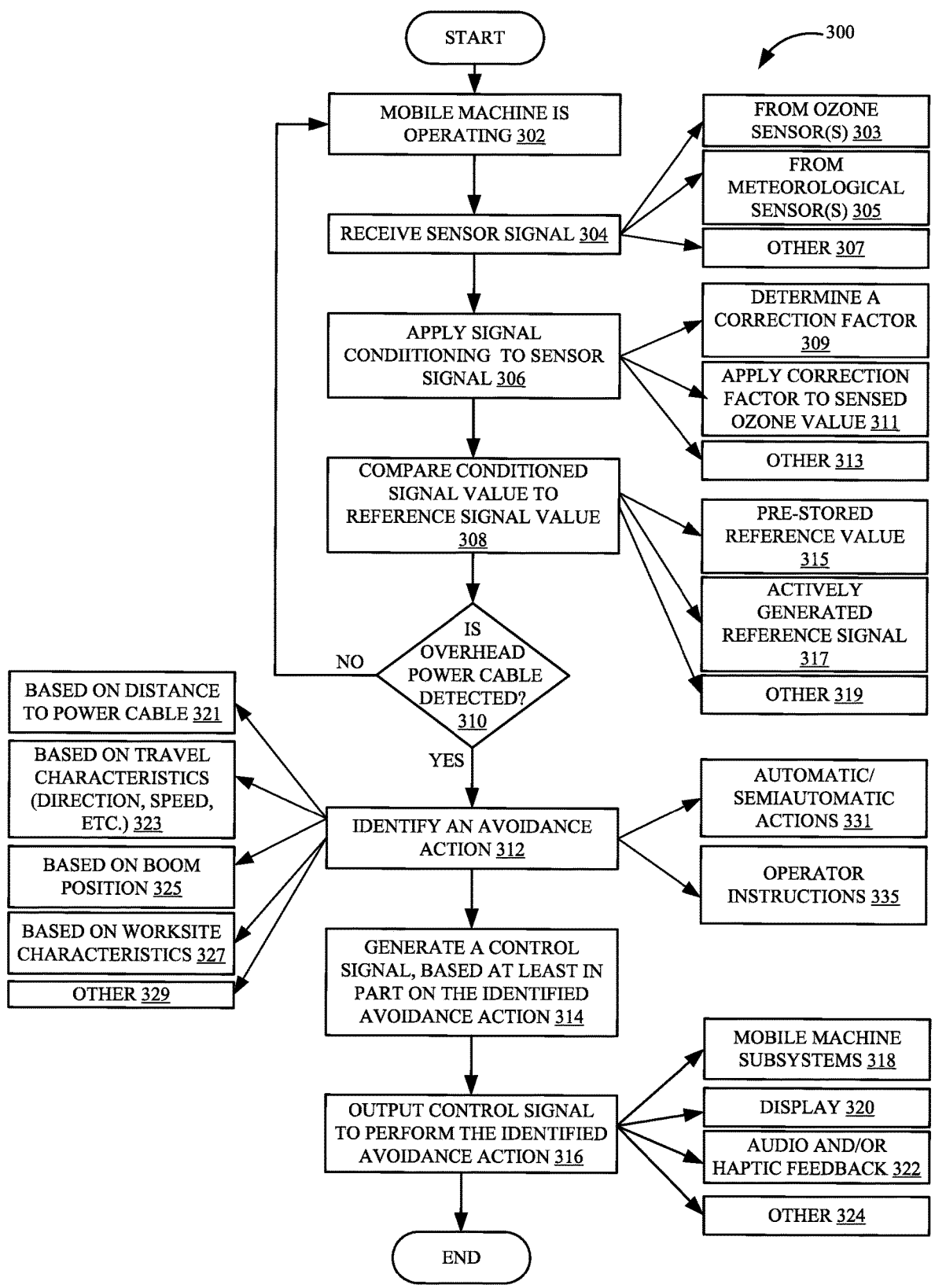
FIG. 3 is a flow diagram of one example operation of detecting an overhead power cable with the overhead power cable avoidance system discussed with respect to the previous FIGS.

FIG. 3 is a flow diagram of one example operation 300 of detecting an overhead power cable with overhead power cable avoidance system 230 discussed with respect to the previous FIGS. FIG. 3 illustratively shows that operation 300 begins when mobile machine 102 is performing an operation, such as a spraying operation at worksite 100, such as a transport operation, a boom deployment operation, etc. This is indicated at block 302.

At block 304, overhead power cable avoidance system 230 receives a sensor signal. For instance, overhead power cable avoidance system 230 can receive a sensor signal generated by power cable sensor(s) 232, which indicates a sensed amount of $O_3$ in the atmosphere. This is indicated by block 303. Overhead power cable avoidance system 230 can also receive sensor signals generated by meteorological sensor(s) 234, as indicated by block 305.

At block 306, signal conditioning logic 240 conditions the received sensor signals. Signal conditioning logic 240 can condition sensor signals in a wide variety of different ways. For instance, conditioning can include amplification, linearizing, normalizing, etc. One particular mechanism for conditioning sensor signals includes monitoring the influence of environmental conditions on measured values of $O_3$ concentration. For example, signal conditioning logic 240 may determine that the most significant impact on measured concentration of $O_3$ near power cables results from variations in temperature, wind speed, and relative humidity, for instance. Signal conditioning logic 240 can obtain meteorological sensor signals generated by meteorological sensor(s) 234 and determine a coefficient (or other correction factor) to be applied to the sensor signals generated by power-cable sensor(s) 232. As such, signal conditioning logic 240 can determine a coefficient (or other correction factor) as indicated by block 309. It can then apply the coefficient to adjust a sensed amount of $O_3$ according to measured environmental conditions as indicated by block 311. Signal conditioning logic 240 can condition the sensor signals in other ways as well, and this is indicated by block 313.

At block 308, power cable detection logic 236 can compare the conditioned sensor signal to a reference signal. A reference signal generally represents a reference concentration of $O_3$. To generate a reference signal, power cable detection logic 236 can identify and obtain a pre-stored value from data store(s) 228. This is indicated by block 315. The pre-stored value can be a threshold value or another value and it can be generated in response to an operator input, or it can be generated automatically or semi-automatically based on a wide variety of other inputs. For instance, a reference value can be stored in association with a particular location identifier that identifies the worksite 100 at which mobile machine 102 is currently operating, or it can be stored in association with historical environmental information that indicates environmental parameters that were measured during a previous operation at worksite 100.

Power cable detection logic 236 can also actively generate a reference signal, indicating a reference concentration of $O_3$, based on a signal generated by a reference sensor. This is indicated by block 317.

FIG. 1B illustratively shows three positions 107-1, 107-2, and 107-3 that power cable sensor(s) 232 can be positioned on mobile machine 102. Positions 107-1 and 107-2 generally represent one or more sampling sensor positions that are more near a position on boom 104 that are more likely to accidently come into contact with a power cable 103 (e.g., they are more near distal ends of elongate positions on arms 112—e.g., portions spaced further from the frame of machine 102), relative to position 107-3 which generally represents one or more reference sensor positions that are positions that are less likely to accidently contact power cable 103 (e.g., they are more near proximal ends of boom 104 that are nearer the frame of mobile machine 102). Thus, positions 107-1 and 107-2 can have power cable sensor(s) 232 that generate signals representing a sample concentration of $O_3$ near a place on boom 104 that may accidently contact power cable 103. Position 107-3 can have power cable sensor(s) 232 that generate signals representing a reference concentration of $O_3$ near mobile machine 102. Because position 107-3 is relatively far away from the ends of arms 112, which are typically the portions of mobile machine 102 that are most at risk for contacting power cables 103, sensor signals obtained from position 107-3 can be used as reference signals (e.g., to determine a reference value representing a reference or control concentration of $O_3$).

The reference $O_3$ value can be generated in other ways as well. This is indicated by block 319.

Power cable detection logic 236 can then compare the reference value (wherever it was obtained from), indicating a reference concentration of $O_3$ in the atmosphere near position 107-3, to a sample sensor signal value, indicating a sample concentration of $O_3$ in the atmosphere near positions 107-1 and 107-2. This is indicated by block 308.

At block 310, power cable detection logic 236 uses the comparison between the conditioned signal and the reference signal to determine whether an overhead power cable is detected. Power cable detection logic 236 can determine that the sample concentration of $O_3$ exceeds the reference concentration of $O_3$ (e.g., the threshold, control value), and in response, automatically detect a presence of an overhead power cable. By way of example only, it may be that if power cable detection logic 236 determines that a sample concentration (say, 150 ppb) of $O_3$ exceeds the reference concentration of (say 110 ppb) of $O_3$, then logic 236 detects an overhead power cable near mobile machine 102, such as near boom 104. In another example, power cable detection logic 236 can identify a relative concentration of $O_3$, of the reference value relative to the sample value based on the comparison between the conditioned sensor signal and the reference signal. This relative concentration can also be compared to a threshold or other reference value in detecting the power cable. If, however, a power cable is not detected, operation 300 illustratively reverts to block 302.

When a power cable is detected at block 310, operation 300 continues at block 312, where avoidance decision logic 238 identifies an avoidance action. At block 312, avoidance decision logic 238 identifies a particular avoidance action from a plurality of possible avoidance actions. For instance, avoidance decision logic 238 can select the particular avoidance action as being the most appropriate action for avoiding contact between mobile machine 102 and power cable 103 and/or supports 101. Avoidance decision logic 238 can take into consideration a determined distance between mobile machine 102 and the detected power cable (as indicated by block 321), travel characteristics (such as a direction that mobile machine 102 is traveling (e.g., indicated by arrow 105 in FIG. 1) when the power cable is detected, the speed of machine 102, etc., (as indicated by block 323), the position of boom 104 (as indicated in block 325), other positioning information obtained by positioning system 254, and information regarding worksite 100 such as a degree of slope, other topology information (as indicated by block 327), among other inputs and information (as indicated by block 329). Each of the avoidance actions identified by avoidance decision logic 238 indicates one or more actions to be implemented by mobile machine 102. These actions can include actions that automatically or semi-automatically control systems and controllable subsystems 212 of mobile machine 102 (as indicated by block 331), they can be actions that instruct operator 248 to perform a task, such as to provide an operator input via user interface mechanisms 224 (as indicated by block 333), or they can be other actions that generally include instructions to control mobile machine 102 for avoiding contact with power cables 103 and/or supports 101. Avoidance decision logic 238 outputs an indication of the identified avoidance action to control signal generator 206.

Control signal generator 206 generates a control signal, to control mobile machine 102, based at least in part on the identified avoidance action. This is indicated by block 314.

Control signal generator 206 outputs the generated control signal to perform the identified avoidance action. This is indicated by block 316. In the illustrated example, the control signal can be output to controllable subsystems 212, as indicated at block 318. For example, the control signal can be output to automatically control propulsion system 214 to stop or change the direction of travel of mobile machine 102 to avoid contacting power cables 103 and/or supports 101. In another example, the control signal can be output to boom deployment system 216 to automatically control actuators that move boom 104 and arms 112. Boom 104 might be in between the deployed position and the travel position (e.g., as shown in FIG. 1B) when an overhead power cable is detected, and in response a control signal is generated and output to automatically lower arm portions 112-3 and 112-4 to a height that will avoid contact with power cables 103 and/or supports 101 as mobile machine 102 continues to travel in the direction generally indicated by arrow 105.

The control signal can also be output to control user interface logic 226, such as by generating a representation of a user interface display for operator view and/or interaction, as indicated at block 320. For example, the control signal can be used to generate a visual map or modify a pictorial representation of worksite 100, and thus it can be used to visually indicate the detected positions of power cables 103 and/or supports 101. The control signal can also be output to provide audio and/or haptic feedback, as indicated by block 322. For example, sounds or vibration can be output through one or more of user interface mechanisms 224 (e.g., vibration feedback through a joystick that receives input from operator 248 to control propulsion system 214 and boom deployment system 216). These and other features can be controlled to generate output signals as indicated at block 324, that either automatically control mobile machine 102 or provide some type of operator-assistance to enhance the operator's understanding of hazardous conditions and how to go about avoiding the hazardous conditions. For instance, other outputs in accordance with block 324 can include other operator assistance features that notify operator 248 of the detected presence of an overhead power cable, and suggest one or more particular actions that operator 248 can implement to safely avoid contact with the cable.

It is noted that while agricultural spraying machines have been particularly discussed with respect to the examples described herein, other machines can also be implemented with said examples. Thus, the present disclosure is not limited to use of the systems and processes discussed with merely spraying machines. They can be used with other machines as well, some of which are mentioned above.

The present discussion has mentioned processors and servers. In one example, the processors and servers include computer processors with associated memory and timing circuitry, not separately shown. They are functional parts of the systems or devices to which they belong and are activated by, and facilitate the functionality of the other components or items in those systems.

Also, a number of user interface displays have been discussed. They can take a wide variety of different forms and can have a wide variety of different user actuatable input mechanisms disposed thereon. For instance, the user actuatable input mechanisms can be text boxes, check boxes, icons, links, drop-down menus, search boxes, etc. They can also be actuated in a wide variety of different ways. For instance, they can be actuated using a point and click device (such as a track ball or mouse). They can be actuated using hardware buttons, switches, a joystick or keyboard, thumb switches or thumb pads, etc. They can also be actuated using a virtual keyboard or other virtual actuators. In addition, where the screen on which they are displayed is a touch sensitive screen, they can be actuated using touch gestures. Also, where the device that displays them has speech recognition components, they can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

Figure 4:
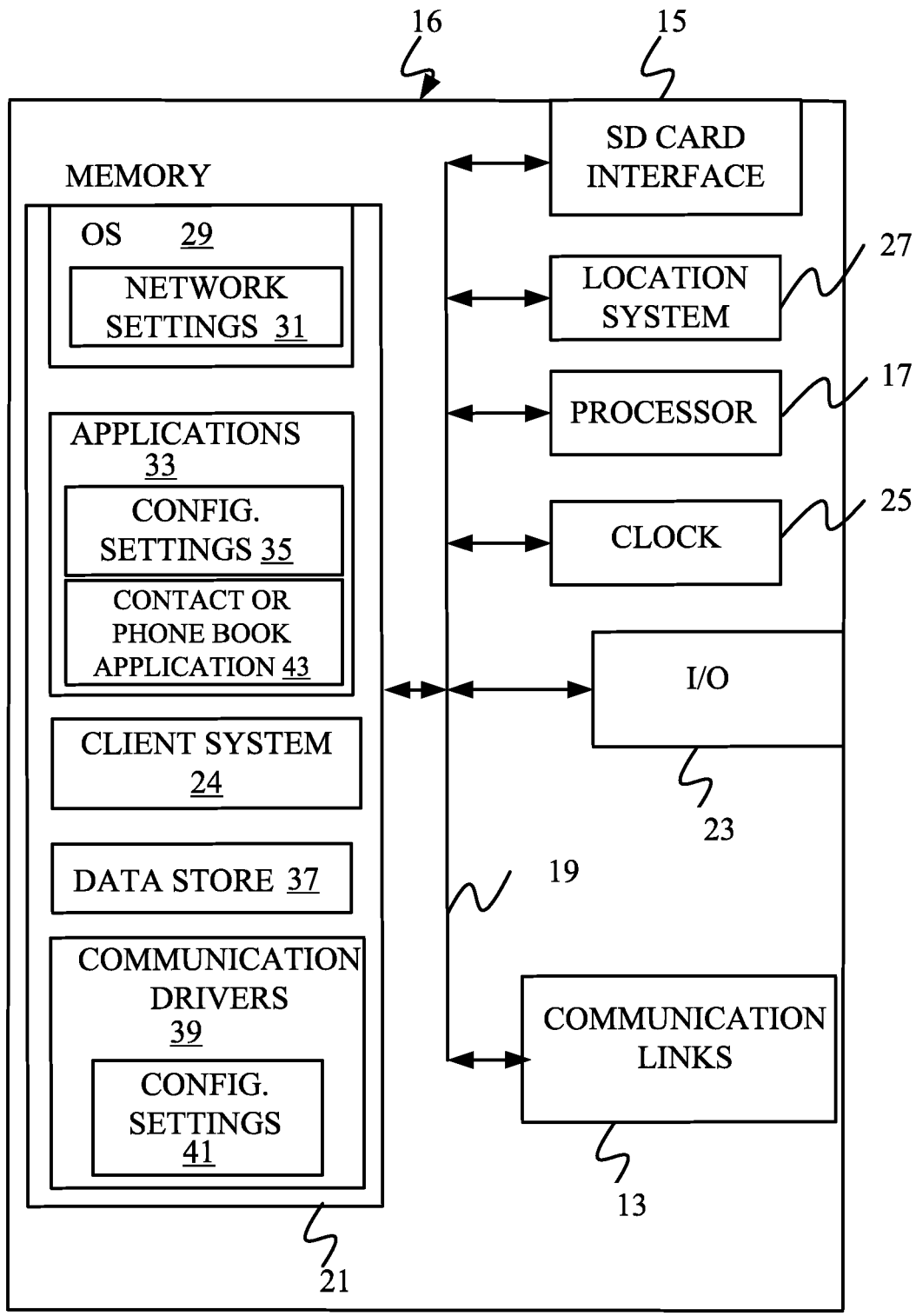
FIGS. 4-6 show examples of mobile devices that can be used in the architectures shown in the previous figures.
Figure 5:
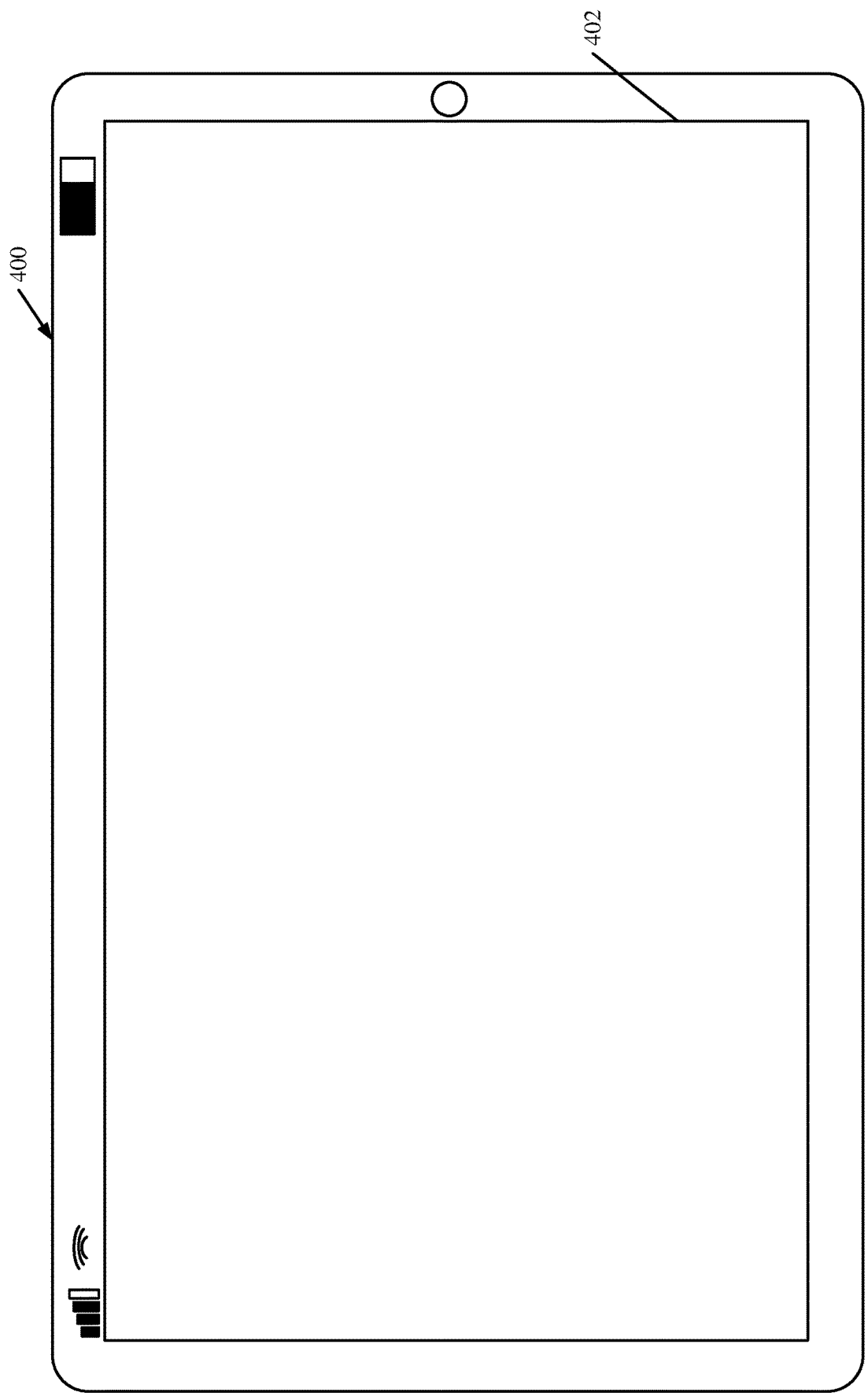
Figure 6:
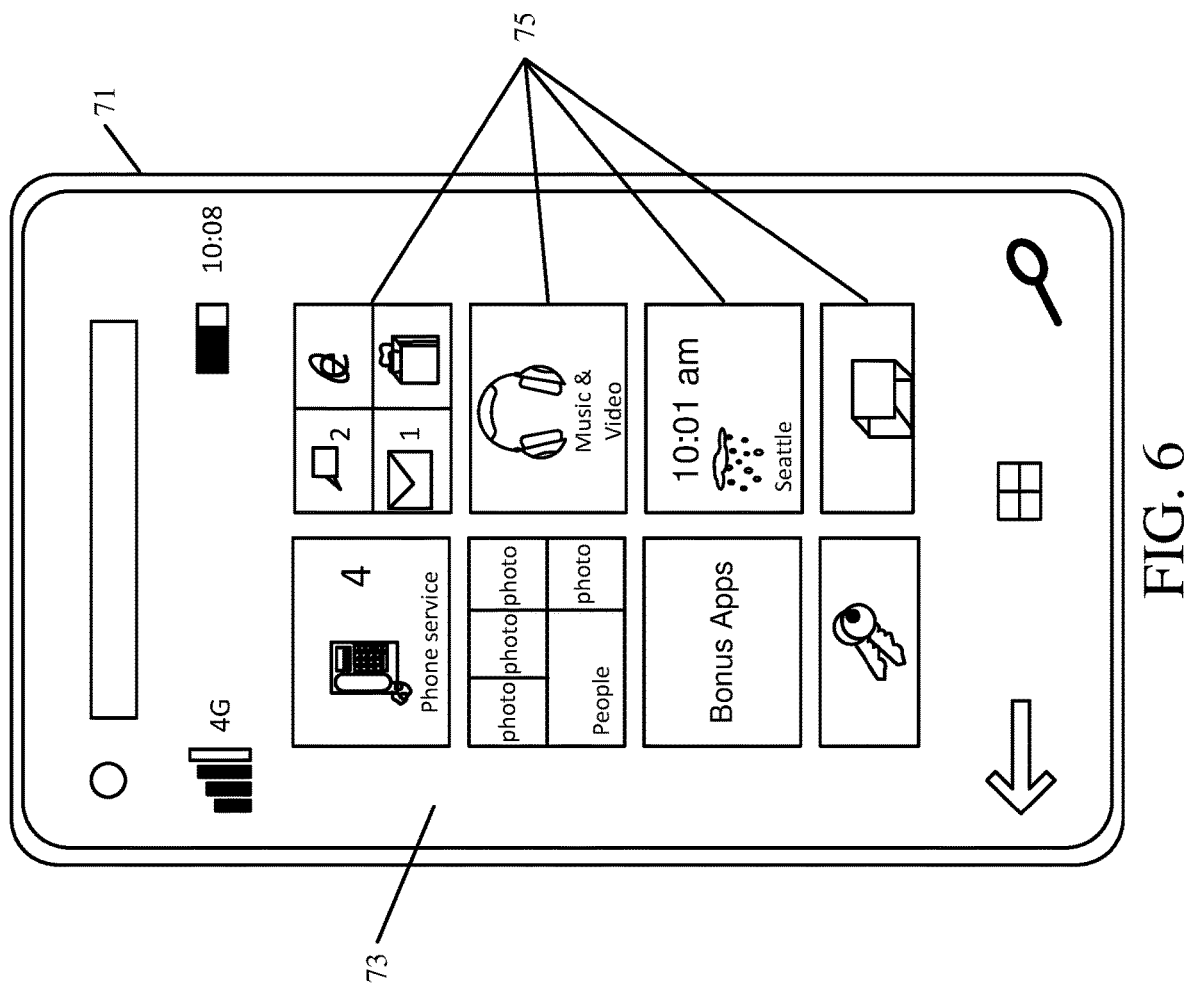

FIG. 4 is a simplified block diagram of one illustrative example of a handheld or mobile computing device that can be used as a user's or client's hand held device 16, in which the present system (or parts of it) can be deployed. For instance, a mobile device can be deployed in computing architecture 200 in the operator compartment of mobile machine 102 or for use in generating, processing, or displaying the information discussed herein and in generating a control interface. FIGS. 5-6 are examples of handheld or mobile devices.

FIG. 4 provides a general block diagram of the components of a client device 16 that can run some components shown in FIG. 2, that interacts with them, or both. In the device 16, a communications link 13 is provided that allows the handheld device to communicate with other computing devices and in some examples provide a channel for receiving information automatically, such as by scanning. Examples of communications link 13 include allowing communication though one or more communication protocols, such as wireless services used to provide cellular access to a network, as well as protocols that provide local wireless connections to networks.

In other examples, applications can be received on a removable Secure Digital (SD) card that is connected to an interface 15. Interface 15 and communication links 13 communicate with a processor 17 (which can also embody processors or servers from previous FIGS.) along a bus 19 that is also connected to memory 21 and input/output (I/O) components 23, as well as clock 25 and location system 27.

I/O components 23, in one embodiment, are provided to facilitate input and output operations. I/O components 23 for various embodiments of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. It can also include computer storage media (described below). Memory 21 stores computer readable instructions that, when executed by processor 17, cause the processor to perform computer-implemented steps or functions according to the instructions. Processor 17 can be activated by other components to facilitate their functionality as well.

FIG. 5 shows one example in which device 16 is a tablet computer 400. In FIG. 5, computer 400 is shown with user interface display screen 402. Screen 402 can be a touch screen or a pen-enabled interface that receives inputs from a pen or stylus. It can also use an on-screen virtual keyboard. Of course, it might also be attached to a keyboard or other user input device through a suitable attachment mechanism, such as a wireless link or USB port, for instance. Computer 400 can also illustratively receive voice inputs as well.

FIG. 6 shows that the device can be a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 7:
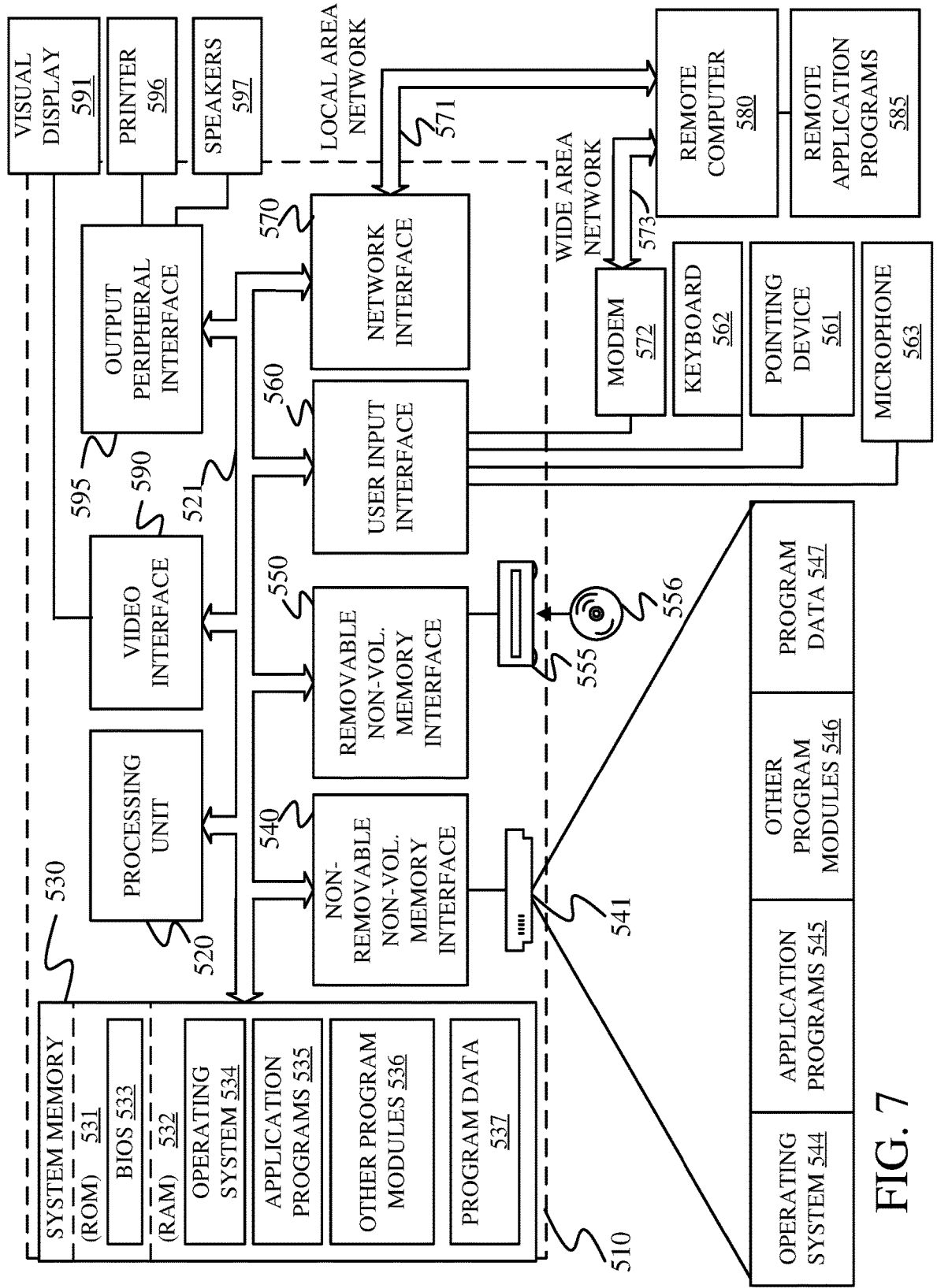
FIG. 7 is a block diagram showing one example of a computing environment that can be used in the architectures shown in the previous figures.

FIG. 7 is one example of a computing environment in which elements of FIG. 2, or parts of it, (for example) can be deployed. With reference to FIG. 7, an example system for implementing some embodiments includes a general-purpose computing device in the form of a computer 510. Components of computer 510 may include, but are not limited to, a processing unit 520 (which can comprise processors or servers from previous FIGS.), a system memory 530, and a system bus 521 that couples various system components including the system memory to the processing unit 520. The system bus 521 may be any of several types of bus structures including a memory bus or memory controller, a peripheral bus, and a local bus using any of a variety of bus architectures. Memory and programs described with respect to FIG. 2 can be deployed in corresponding portions of FIG. 7.

Computer 510 typically includes a variety of computer readable media. Computer readable media can be any available media that can be accessed by computer 510 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 510. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 530 includes computer storage media in the form of volatile and/or nonvolatile memory such as read only memory (ROM) 531 and random access memory (RAM) 532. A basic input/output system 533 (BIOS), containing the basic routines that help to transfer information between elements within computer 510, such as during start-up, is typically stored in ROM 531. RAM 532 typically contains data and/or program modules that are immediately accessible to and/or presently being operated on by processing unit 520. By way of example, and not limitation, FIG. 7 illustrates operating system 534, application programs 535, other program modules 536, and program data 537.

The computer 510 may also include other removable/non-removable volatile/nonvolatile computer storage media. By way of example only, FIG. 7 illustrates a hard disk drive 541 that reads from or writes to non-removable, nonvolatile magnetic media, an optical disk drive 555, and nonvolatile optical disk 556. The hard disk drive 541 is typically connected to the system bus 521 through a non-removable memory interface such as interface 540, and optical disk drive 555 are typically connected to the system bus 521 by a removable memory interface, such as interface 550.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 7, provide storage of computer readable instructions, data structures, program modules and other data for the computer 510. In FIG. 7, for example, hard disk drive 541 is illustrated as storing operating system 544, application programs 545, other program modules 546, and program data 547. Note that these components can either be the same as or different from operating system 534, application programs 535, other program modules 536, and program data 537.

A user may enter commands and information into the computer 510 through input devices such as a keyboard 562, a microphone 563, and a pointing device 561, such as a mouse, trackball or touch pad. Other input devices (not shown) may include a joystick, game pad, satellite dish, scanner, or the like. These and other input devices are often connected to the processing unit 520 through a user input interface 560 that is coupled to the system bus, but may be connected by other interface and bus structures. A visual display 591 or other type of display device is also connected to the system bus 521 via an interface, such as a video interface 590. In addition to the monitor, computers may also include other peripheral output devices such as speakers 597 and printer 596, which may be connected through an output peripheral interface 595.

The computer 510 is operated in a networked environment using logical connections (such as a local area network—LAN, or wide area network WAN) to one or more remote computers, such as a remote computer 580.

When used in a LAN networking environment, the computer 510 is connected to the LAN 571 through a network interface or adapter 570. When used in a WAN networking environment, the computer 510 typically includes a modem 572 or other means for establishing communications over the WAN 573, such as the Internet. In a networked environment, program modules may be stored in a remote memory storage device. FIG. 7 illustrates, for example, that remote application programs 585 can reside on remote computer 580.

It should also be noted that the different examples described herein can be combined in different ways. That is, parts of one or more examples can be combined with parts of one or more other examples. All of this is contemplated herein.

Example 1 is a mobile machine comprising:
a sensor that generates a sensor signal indicative of ozone gas concentration;
power cable detection logic that receives the sensor signal and, based on the received sensor signal, determines that a power cable is proximate the mobile machine;
avoidance decision logic that identifies an avoidance action in response to determining that the power cable is proximate the mobile machine; and a control signal generator that generates a control signal based on the avoidance action.

Example 2 is the mobile machine of any or all previous examples, further comprising:
a mechanical assembly operably coupled to the mobile machine;
a deployment system that moves the mechanical assembly between a deployed position in which it is extended away from the mobile machine, and a transport position, in which it is retracted toward the mobile machine; and
wherein the control signal generator generates the control signal to control the boom deployment system.

Example 3 is the mobile machine of any or all previous examples, wherein the control signal generator is configured to control the deployment system to avoid contact between the mechanical assembly and the power cable.

Example 4 is the mobile machine of any or all previous examples, wherein the control signal generator is configured to control the deployment system to stop moving the mechanical assembly between the deployed position and the transport position.

Example 5 is the mobile machine of any or all previous examples, further comprising:
signal conditioning logic configured to condition the sensor signal based on an additional sensed signal.

Example 6 is the mobile machine of any or all previous examples, wherein the additional sensed signal is indicative of a sensed meteorological parameter, and wherein the signal conditioning logic is configured to condition the sensor signal, indicative of ozone gas concentration, based on the sensed meteorological parameter.

Example 7 is the mobile machine of any or all previous examples, wherein the power cable detection logic is configured to compare the sensor signal to a reference signal generated by an additional sensor.

Example 8 is the mobile machine of any or all previous examples, wherein the mobile machine includes a vehicle frame and wherein the mechanical assembly has a proximal end relative to the frame and a distal end relative to the frame and wherein the sensor is disposed on the mobile machine at a first position and the additional sensor is disposed on the mobile machine at a second position, the first position being nearer the distal end of the mechanical assembly than the second position.

Example 9 is the mobile machine of any or all previous examples, wherein the power cable detection logic is configured to determine a concentration of ozone gas near the boom based on the comparison between the sensor signal and the reference signal.

Example 10 is the mobile machine of any or all previous examples, wherein the power cable detection logic determines that the power cable is proximate the mechanical assembly based on the concentration of ozone gas.

Example 11 is the mobile machine of any or all previous examples, and further comprising:
a steering and propulsion system, wherein the control signal generated by the control signal generator is output to control the steering propulsion system on the mobile machine, based on the identified avoidance action.

Example 12 is a computer-implemented method, comprising:
receiving a sensor signal indicative of ozone gas concentration;
based on the sensor signal, determining that an overhead power cable is proximate a mobile machine operating at a worksite; and generating an action signal that controls the mobile machine to perform an action in response to determining that the overhead power cable is proximate the mobile machine.

Example 13 is the computer-implemented method of any or all previous examples, wherein generating an action signal comprises:

generating the action signal to control a propulsion system of the mobile machine to move the mobile machine to avoid contact between the mobile machine and the power cable.

Example 14 is the computer-implemented method of any or all previous examples, wherein the machine includes a mechanical assembly, movably coupled to a frame of the mobile machine and a deployment system that moves the mechanical assembly between a deployed position and a travel position and wherein generating an action signal comprises:

generating the action signal to control the deployment system of the mobile machine to move the mechanical assembly to avoid contacting the overhead power cable.

Example 15 is the computer-implemented method of any or all previous examples, wherein determining that the overhead power cable is proximate the mobile machine comprises:

identifying a concentration metric indicative of a concentration of ozone gas, based on the sensor signal;
comparing the concentration metric to a threshold concentration of ozone gas; and
in response to determining that the concentration metric meets the threshold concentration of ozone gas, determining that the overhead power cable is proximate the mobile machine.

Example 16 is the computer-implemented method of any or all previous examples, further comprising:

determining a distance between the overhead power cable and the mobile machine, based on the sensor signal.

Example 17 is the computer-implemented method of any or all previous examples, wherein generating an action signal that controls the mobile machine to perform an action comprises:

generating an action signal that controls at least one of direction of movement or speed of movement of the mobile machine based at least in part on the determined distance between the overhead power cable and the mobile machine.

Example 18 is a mobile spraying machine, comprising:
a boom;
a sensor configured to generate a sensor signal indicative of an ozone gas concentration;
power cable detection logic that receives the sensor signal and, based on the received sensor signal, detects an overhead power cable;
avoidance decision logic that identifies an avoidance action to avoid contact between the boom and the overhead power cable; and
a control signal generator that generates a control signal based on the identified avoidance action, and outputs the control signal to control the mobile spraying machine, to implement the avoidance action.

Example 19 is the mobile spraying machine of any or all previous examples, wherein the power cable detection logic is configured to compare a sensed concentration of ozone gas proximate the boom to a threshold concentration of ozone gas, and based on the comparison, detect the overhead power cable.

Example 20 is the mobile spraying machine of any or all previous examples, wherein the power cable detection logic identifies a distance between the overhead power cable and the boom and wherein the avoidance decision logic is configured to identify the avoidance action based on the distance between the detected overhead power cable and the boom.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A mobile machine comprising:
a vehicle frame;
a mechanical assembly having a proximal end relative to the vehicle frame and a distal end relative to the vehicle frame;
a first ozone sensor that generates a first sensor signal indicative of ozone gas concentration within a sensing distance of the first ozone sensor;
a second ozone sensor that generates a second sensor signal indicative of ozone gas concentration within a sensing distance of the second ozone sensor;
a processor configured to execute a set of instructions that cause the processor to provide:
power cable detection that detects presence of an overhead power cable within the sensing distance of either the first ozone sensor or the second ozone sensor based on a difference between the first sensor signal indicative of ozone gas concentration and the second sensor signal indicative of ozone gas concentration;
avoidance action identification that identifies an avoidance action in response to detecting the presence of the overhead power cable; and
control signal generation that generates a control signal based on the avoidance action; and
wherein the first ozone sensor is disposed on the mobile machine at a first position and the second ozone sensor is disposed on the mobile machine at a second position, a distance of the first position from the distal end of the mechanical assembly being less than a distance of the second position from the distal end.

2. The mobile machine of claim 1, further comprising:
a deployment system that moves the mechanical assembly between a deployed position in which it is extended away from the mobile machine, and a transport position in which it is retracted toward the mobile machine; and
wherein the control signal generation generates the control signal to control the deployment system.

3. The mobile machine of claim 2, wherein the control signal is configured to control the deployment system to avoid contact between the mechanical assembly and the overhead power cable.

4. The mobile machine of claim 3 wherein the control signal is configured to control the deployment system to stop moving the mechanical assembly between the deployed position and the transport position.

5. The mobile machine of claim 1, wherein the set of instructions cause the processor to further provide:
signal conditioning configured to condition the first sensor signal indicative of ozone gas concentration and the second sensor signal indicative of ozone gas concentration, based on an additional sensed signal.

6. The mobile machine of claim 5, wherein the additional sensed signal is indicative of a sensed meteorological parameter, and wherein the signal conditioning is configured to condition the first sensor signal indicative of ozone gas concentration and the second sensor signal indicative of ozone gas concentration, based on the sensed meteorological parameter.

7. The mobile machine of claim 1, wherein the power cable detection is configured to, based on the difference between the first sensor signal indicative of ozone gas concentration and the second sensor signal indicative of ozone gas concentration, determine a position of the detected power cable relative to the mobile machine.

8. The mobile machine of claim 7, wherein the power cable detection is configured to determine a position of the detected power cable relative to the mechanical assembly, wherein the control signal controls the mobile machine to avoid contact between the mechanical assembly and the detected power cable.

9. The mobile machine of claim 1, and further comprising: a steering and propulsion system, wherein the control signal is output to control the steering propulsion system on the mobile machine, based on the avoidance action.

10. A computer-implemented method, comprising:
receiving a first sensor signal indicative of ozone gas concentration from a first ozone sensor disposed at first position on a mobile machine having a vehicle frame and a mechanical assembly;
receiving a second sensor signal indicative of ozone gas concentration from a second ozone sensor disposed on the mobile machine at a second position, wherein the distance of the first position from a distal end of the mechanical assembly is less than a distance of the second position from the distal end;
identifying a first concentration metric indicative of a first concentration of ozone gas, based on the first sensor signal;
identifying a second concentration metric indicative of a second concentration of ozone gas, based on the second sensor signal;
comparing the first concentration metric to the second concentration metric to determine a difference between the first concentration metric and the second concentration metric;
detecting presence of an overhead power cable within an area around a mobile machine operating at a worksite based on the difference between the first concentration metric and the second concentration metric; and
generating an action signal that controls the mobile machine to perform an action in response to detecting the presence of the overhead power cable.

11. The computer-implemented method of claim 10, wherein generating the action signal comprises:
generating the action signal to control a propulsion system of the mobile machine to move the mobile machine to avoid contact between the mobile machine and the overhead power cable.

12. The computer-implemented method of claim 10, wherein the mechanical assembly is movably coupled to the frame of the mobile machine, wherein the distal end is distal relative to the vehicle frame and further includes a proximal end, proximal relative to the vehicle frame, the mobile machine further comprising;
a deployment system that moves the mechanical assembly between a deployed position and a travel position and wherein generating the action signal comprises:
generating the action signal to control the deployment system of the mobile machine to move the mechanical assembly to avoid contacting the overhead power cable.

13. The computer-implemented method of claim 10, further comprising:
determining a distance between the overhead power cable and the mobile machine, based on the first and second sensor signals.

14. The computer-implemented method of claim 13, wherein generating an action signal that controls the mobile machine to perform an action comprises: generating an action signal that controls at least one of direction of movement or speed of movement of the mobile machine based at least in part on the determined distance between the overhead power cable and the mobile machine.

15. The computer-implemented method of claim 13, wherein determining the distance between the overhead power cable and the mobile machine comprises:
determining a distance between the overhead power cable and the mechanical assembly.

16. The computer-implemented method of claim 15, generating an action signal that controls the mobile machine to perform an action comprises:
generating the action signal to control the mobile machine to perform an action to avoid contact between the overhead power cable and the mechanical assembly, based at least in part on the determined distance between the overhead power cable and the mechanical assembly.

17. A mobile spraying machine, comprising:
a boom;
a first sensor located at a first position on the boom and configured to generate a first sensor signal indicative of a first ozone gas concentration within a sensing distance of the first sensor;
a second sensor located at a second position on the boom and configured to generate a second sensor signal indicative of a second ozone gas concentration within a sensing distance of the second sensor; and
a processor configured to execute a set of instructions that cause the processor to provide:
power cable detection configured to detect presence of an overhead power cable within the sensing distance of either the first sensor or the second sensor based on a difference between the first sensor signal indicative of the first ozone gas concentration and the second sensor signal indicative of the second ozone gas concentration;
avoidance action identification that identifies an avoidance action to avoid contact between the boom and the overhead power cable; and
control signal generation that generates a control signal based on the identified avoidance action, and outputs the control signal to control the mobile spraying machine, to implement the avoidance action.

18. The mobile spraying machine of claim 17, wherein the power cable detection is configured to determine a difference between the first ozone gas concentration and the second ozone gas concentration based on the comparison of the first sensor signal and the second sensor signal, and, based on the difference, detect the position of the overhead power cable relative to the mobile machine.

19. The mobile spraying machine of claim 17, wherein the power cable detection identities a distance between the overhead power cable and the boom and wherein the avoidance action identification is configured to identify the avoidance action based on the distance between the detected overhead power cable and the boom.

* * * * *

UNITED STATES PATENT AND TRADEMARK OFFICE
CERTIFICATE OF CORRECTION

PATENT NO. : 11,150,648 B2
APPLICATION NO. : 15/943849
DATED : October 19, 2021
INVENTOR(S) : Paresh Bharatiya and Shruti Dev It is certified that error appears in the above-identified patent and that said Letters Patent is hereby corrected as shown below:

On the Title Page

Item (73) "Assignee: Deere & Company, a Delaware Corporation, Moline, IL (US)" should be added.

Signed and Sealed this
First Day of November, 2022

Katherine Kelly Vidal
*Director of the United States Patent and Trademark Office*